United States Patent
Schnitzler et al.

(10) Patent No.: US 9,510,889 B2
(45) Date of Patent: *Dec. 6, 2016

(54) APPARATUS FOR COAGULATING TISSUE

(71) Applicant: ERBE ELEKTROMEDIZIN GMBH, Tuebingen (DE)

(72) Inventors: Uwe Schnitzler, Tuebingen (DE); Daniel Schaeller, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/304,513

(22) Filed: Jun. 13, 2014

(65) Prior Publication Data

US 2014/0296851 A1    Oct. 2, 2014

Related U.S. Application Data

(63) Continuation of application No. 13/838,887, filed on Mar. 15, 2013, now abandoned, which is a (Continued)

(30) Foreign Application Priority Data

Oct. 30, 2003 (DE) .................... 103 50 709

(51) Int. Cl.
*A61B 18/14* (2006.01)
*A61B 18/04* (2006.01)
*A61B 18/00* (2006.01)

(52) U.S. Cl.
CPC ............. *A61B 18/042* (2013.01); *A61B 18/14* (2013.01); *A61B 2018/00196* (2013.01); (Continued)

(58) Field of Classification Search
CPC .................... A61B 18/042; A61B 2018/00583
(Continued)

(56) References Cited

U.S. PATENT DOCUMENTS 2,828,748 A   4/1958   August
5,088,997 A   2/1992   Delahuerga et al.
(Continued)

FOREIGN PATENT DOCUMENTS

DE    41 39 029         6/1993
DE    691 26 721 T2    10/1997
(Continued)

OTHER PUBLICATIONS

Machine Translation of JP 2002-301088-A, Printed Oct. 19, 2010.
Translation of JP 2002301088 from Nov. 2011, original Japanese patent published Aug. 15, 2002, pp. 1-41.

*Primary Examiner* — Ronald Hupczey, Jr.
(74) *Attorney, Agent, or Firm* — Blank Rome LLP

(57) ABSTRACT

An apparatus for coagulating tissue, including a gas-delivering device for delivering a plasma comprised of an ionized inert gas from the outlet of the gas-delivering device, an electrode adapted to supply a high-frequency current that projects out of the gas-delivering device and a guiding device disposed at a distal end of the electrode. The relative configuration of the outlet of the gas-delivering device and the guiding device are such that the plasma (and an electric arc) can be directed in any direction 360° with respect to the outlet of the gas-delivering device. The plasma is directed along a path of least electric resistance, thus causing the plasma to be directed to a tissue to be treated, regardless of a position of the tissue relative to a rotational position of the outlet of the gas-delivering device.

28 Claims, 1 Drawing Sheet

Related U.S. Application Data continuation-in-part of application No. 10/577,297, filed as application No. PCT/EP2004/012212 on Oct. 28, 2004.

(52) U.S. Cl.
CPC .............. *A61B 2018/00583* (2013.01); *A61B 2018/00589* (2013.01); *A61B 2018/00601* (2013.01); *A61B 2018/00607* (2013.01); *A61B 2018/00791* (2013.01); *A61B 2018/1475* (2013.01)

(58) Field of Classification Search
USPC ................................ 606/31–50; 607/115–116
See application file for complete search history.

(56) References Cited

U.S. PATENT DOCUMENTS

| | | | |
|---|---|---|---|
| 5,244,462 A | 9/1993 | Delahuerga et al. | |
| 5,449,356 A | 9/1995 | Walbrink et al. | |
| 5,797,856 A * | 8/1998 | Frisbie | A61M 25/09 600/585 |
| 5,902,328 A | 5/1999 | LaFontaine et al. | |
| 6,039,736 A | 3/2000 | Platt, Jr. | |
| 6,112,123 A | 8/2000 | Kelleher et al. | |
| 6,142,995 A | 11/2000 | Cosmescu | |
| 6,149,648 A | 11/2000 | Cosmescu | |
| 6,197,026 B1 | 3/2001 | Farin et al. | |
| 6,602,249 B1 | 8/2003 | Stoddard et al. | |
| 2003/0065324 A1 | 4/2003 | Platt | |
| 2013/0274742 A1 | 10/2013 | Schnitzler et al. | |

FOREIGN PATENT DOCUMENTS

| | | |
|---|---|---|
| DE | 198 20 240 | 12/1999 |
| JP | 2002-301088 A | 10/2002 |

* cited by examiner

APPARATUS FOR COAGULATING TISSUE

CROSS-REFERENCE TO RELATED APPLICATIONS

This application is a continuation of U.S. application Ser. No. 13/838,887, filed Mar. 15, 2013 and now abandoned, which is a continuation-in-part of U.S. application Ser. No. 10/577,297, filed on Apr. 27, 2006, which is a 371 of PCT/EP04/12212, filed on Oct. 28, 2004, which claims priority to German application no. 103 50 709.4, filed Oct. 30, 2003, the subject matter of each of which is incorporated in its entirety by reference herein.

FIELD OF THE INVENTION

The invention relates to an apparatus for coagulating tissue.

BACKGROUND

Such an apparatus is known, for instance, from document DE 41 390 29 A1. In this apparatus, a gas flows axially from an outflow opening of a gas-delivering device to an electrode, and the electrode is positioned in front of the opening, so that a plasma tends to be produced in a direction axial to the gas-delivering device. Especially when an endoscopic operation is being performed within a body cavity, i.e. under confined conditions, it is difficult to coagulate tissue sites situated at the side, in a direction radial with respect to the opening.

The document DE 198 202 40 C2 discloses a tissue-coagulating apparatus in which the electrode is disposed entirely within a tubular probe provided with a slit-shaped opening that passes helically around its circumference, so that the delivered gas and also the plasma emerge in a direction radial to the probe. One problem here resides in manufacturing such probes, in view of the confined spatial relationships. Another is that the probe material can relatively easily be damaged by the high temperatures of the plasma.

SUMMARY

It is an object of the disclosed embodiments to provide an apparatus for coagulating tissue such that, by simple means, it becomes possible reliably to specify a direction of the plasma beam, and thus of the electric arc when a high-frequency current is supplied, that deviates from an axial direction of the apparatus.

This object is achieved by an apparatus according to the present disclosed embodiments. One example embodiment includes a high-frequency generator, an electrode connected to the high-frequency generator and adapted to produce a high-frequency current, a gas-delivering device defining an outlet and adapted to deliver, in use, an inert gas from the outlet of the gas-delivering device into a space defined between the electrode and the tissue such that between the electrode and the tissue a plasma is produced, a distal end of the electrode projecting out of the gas-delivering device, and a guiding device for directing and guiding at least one of the gas and the plasma is disposed at the distal end of the electrode and adapted such that at least a part of the at least one flowing gas and plasma is diverted into a predetermined direction.

Another example embodiment includes a high-frequency generator, an electrode connected to the high-frequency generator and adapted to produce a high-frequency current, a gas-delivering device defining an outlet and adapted to deliver, in use, an inert gas from the outlet of the gas-delivering device into a space defined between the electrode and the tissue. When the inert gas is ionized, a plasma is produced and when a high-frequency current is supplied, an electric arc is produced between the electrode and the tissue. A distal end of the electrode projects out of the gas-delivering device and includes a guiding device disposed thereon. The guiding device directs and guides the plasma (and thus the electric arc) such that it is diverted into a predetermined direction or directions.

Another example embodiment includes an apparatus for coagulating tissue that includes a gas-delivering device defining an outlet and adapted to deliver, in use, a plasma comprised of an ionized inert gas from the outlet of the gas-delivering device, an electrode adapted to supply a high-frequency current, a distal end of the electrode projecting out of the gas-delivering device and a guiding device disposed at a distal end of the electrode. The outlet of the gas-delivering device and the guiding device are adapted such that at least a portion of the plasma is directed to a tissue to be treated, regardless of a position of the tissue relative to a rotational position of the outlet of the gas-delivering device.

Another example embodiment includes an apparatus for coagulating tissue that includes a gas-delivering device defining an outlet and adapted to deliver, in use, a plasma comprised of an ionized inert gas from the outlet of the gas-delivering device, an electrode adapted to supply a high-frequency current, a distal end of the electrode projecting out of the gas-delivering device and a guiding device disposed at a distal end of the electrode. The outlet of the gas-delivering device and the guiding device are adapted such that when a high-frequency current is supplied to the plasma, an electric arc can be formed in any direction 360° with respect to the outlet of the gas-delivering device.

Another example embodiment includes an apparatus for coagulating tissue that includes a gas-delivering device defining an outlet and adapted to deliver, in use, a plasma comprised of an ionized inert gas from the outlet of the gas-delivering device, an electrode adapted to supply a high-frequency current, a distal end of the electrode projecting out of the gas-delivering device and a guiding device disposed at a distal end of the electrode. The outlet of the gas-delivering device and the guiding device are adapted such that the plasma can be directed in any direction 360° with respect to the outlet of the gas-delivering device. This is because the plasma is directed along a path of least electric resistance, causing the plasma to be directed to a tissue to be treated, regardless of a position of the tissue relative to a rotational position of the outlet of the gas-delivering device.

The success of the disclosed embodiments resides in the fact that the electrode itself is structurally included in the overall mechanical construction of the device, in that it to some extent carries part of the gas-delivering device, namely the guiding device. In other words, the guiding device may be supported by the electrode. The preferred direction of the gas/plasma (and thus the electric arc) is thus determined by the guiding device. It should be pointed out here that within a space completely filled with an inert gas, the direction in which the plasma is generated is not influenced by flow of the gas. However, because the plasma (and thus the electric arc) always appears along the path of least overall resistance (e.g., shortest path), and it is practically impossible for the space to be filled entirely homogeneously, even in a body cavity (this is because, for example, a. either air insufflation or $CO_2$ insufflation is used to distend the lumen for visualization, b. some organ lumens are relatively large and will not be homogeneously filled, i.e. the stomach, and/or c. suction and irrigation is frequently utilized along with the coagulation procedure), on one hand, it is possible to specify the gas current and hence the gas concentration within the space using the guiding device, and, on the other hand, the desired change of direction can be brought about by an extension of the path the plasma (and thus the electric arc) must follow from the electrode to the tissue.

Preferably, the guiding device consists of an electrically insulating material, as a result of which the above-mentioned change of path is facilitated.

Furthermore, the guiding devices preferably are made of a thermally stable material, so that during an operation, even if the guiding device is in prolonged contact with the plasma, there are no damaging alterations of the material. A particularly suitable material is a ceramic, which can be applied for instance by spraying on or by dipping. Due to the material of which it is formed, the guiding device may be formed to be in direct contact with the electrode.

The electrode is preferably constructed in the form of a rod or wire, as is known in the art, while the guiding device is preferably disposed in an axially symmetric manner around the electrode, in such a way that the gas/plasma flows into the surrounding space substantially radially with respect to the outlet of the gas-delivering device. This arrangement makes it unnecessary for the apparatus to be rotated within a body cavity during an endoscopic operation in order to coagulate regions of tissue situated radial to the outlet. All that is needed is to bring the apparatus into the vicinity of the tissue site to be coagulated, because the plasma seeks out the lowest-resistance (e.g., shortest) path. The plasma current does not change direction until the plasma path is lengthened, when the treated tissue dries out and hence in turn acquires a higher resistance. This arrangement allows for electric arcing at any direction 360° around the probe. Thus, tissue can be treated in any direction (e.g., 360° around the probe) without the need for probe manipulation (e.g., no need to rotate the probe itself).

The guiding device is preferably made concave on its side that faces the outlet, as a result of which a diversion of the gas stream that favors its flow is accomplished in an especially simple manner. This concave surface of the guiding device diverts the gas in such a way to create a gas flow that extends (substantially) perpendicularly to the longitudinal axis of the gas-delivering device/probe.

To prevent mechanical injury caused by touching the tissue, the guiding device is rounded on its side that faces away from the outlet. The guiding device thus simultaneously constitutes a form of protection against direct contact between electrode and tissue, which could have fatal consequences, as is well known.

In one preferred embodiment, the electrode is movable relative to the outlet, in such a way that when it is in a retracted state, the guiding device closes the outlet in a substantially leakproof manner. This can ensure that during probe introduction no body fluid or other contaminants can enter the gas-delivering device.

BRIEF DESCRIPTION OF THE DRAWINGS

In the following, preferred embodiments are described in greater detail and by way of example with reference to the accompanying drawings.

DETAILED DESCRIPTION OF PREFERRED EMBODIMENTS

Figure 1:
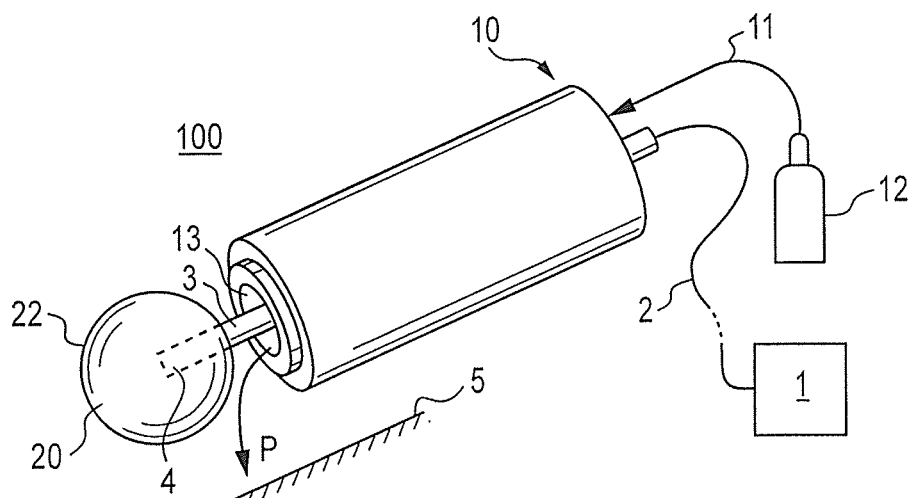
FIG. 1 shows a perspective view of a first preferred embodiment, with peripheral devices indicated schematically.

In the following description, the same reference numerals are used for identical parts or parts with identical actions.

FIG. 1 shows an end piece of a probe 100, comprising a gas-delivering device 10 in the shape of a tube, the lumen of which communicates with a gas source 12 by way of a conduit 11. An electrode 3 (ordinarily made of tungsten) is disposed substantially coaxially within the gas-delivering device 10, and is connected to a high-frequency generator 1 by way of an electrical conductor 2. A distal end 4 of the electrode 3 projects outward through an outlet 13 of the gas-delivering device. In use, a stream of inert gas is supplied by the gas source 12 and emerges from the outlet 13 of the gas-delivering device 10. When this inert gas stream is ionized, a plasma is produced, and when a high-frequency current is supplied to the electrode 3 by the high-frequency generator 1, an electric arc is produced through the plasma between the electrode 3 and the tissue 5. The electric arc may follow generally the same path as the plasma.

A guiding device 20 is attached to the distal end 4 of the electrode 3. In the embodiment shown in FIG. 1, the guiding device is a spherical ceramic part. The guiding device 20 may be supported by the electrode 3. The guiding device 20 may be formed to be in direct contact with the electrode 3. The stream of inert gas, supplied by the gas source 12 and emerging from the outlet 13, is diverted by the guiding device 20 into the direction indicated by the arrow P. It should be recognized that although there is only a single arrow P shown in each of the figures to represent the flow of the gas/plasma, the inert gas/plasma (if the gas is ionized) exits the outlet 13 in a 360° manner around the outlet 13/guiding device 20. If the distal end of probe 100 is positioned near and parallel to a tissue surface 5, the space delimited by the guiding device 20 in combination with the end-region of the gas-delivering device 10, at its outlet 13, is restricted sufficiently that when the supplied inert gas is ionized by a high-frequency current coming from the generator 1, the shortest path available to the resulting plasma between the electrode 3 and the tissue surface 5 is oriented radially with respect to the electrode 3. As a result, the guiding device 20 serves not only to determine the direction of flow of the supplied inert gas, but also to "guide" the plasma (and thus the electric arc) to the tissue surface 5 to be treated.

The configuration of the guiding device 20 allows for electric arcing to occur at any direction 360° around the probe 100. In other words, the electric arc can go in any direction as it exits the outlet 13 of gas-delivering device 10, thus allowing treatment of the closest target tissue in any direction 360° around the probe 100. Since the inert gas exits the outlet 13 in a 360° manner around the outlet 13/guiding device 20, the probe 100 merely can be positioned near the tissue surface 5 without specific relative rotation of the probe 100. Because the plasma will follow the shortest path available, the plasma (and thus the electric arc) will automatically be directed to the tissue surface 5, without the need to rotate the probe 100 to direct the plasma toward the tissue surface 5.

Figure 2:
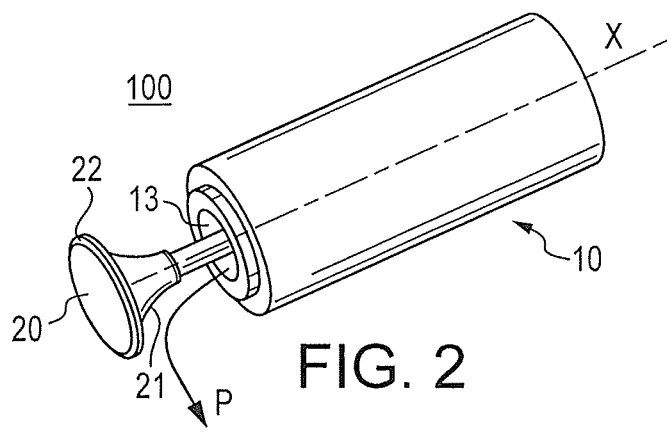
FIG. 2 shows a second preferred embodiment, in a drawing similar to that in FIG. 1.

The embodiment shown in FIG. 2 differs from the embodiment in FIG. 1 in that the guiding device 20 is not spherical but rather is shaped like a valve for an internal combustion engine, comprising a concave inner section 21 in the region opposite the outlet 13 of the gas-delivering device 10. The distal end of the guiding device 20, facing away from the gas-delivering device 10, is flattened. The transitional region between the flattened distal section and the inner section 21 has a rounded contour 22 such that no mechanical damage to the tissue can be caused by contact with the tissue surface 5.

Figure 3:
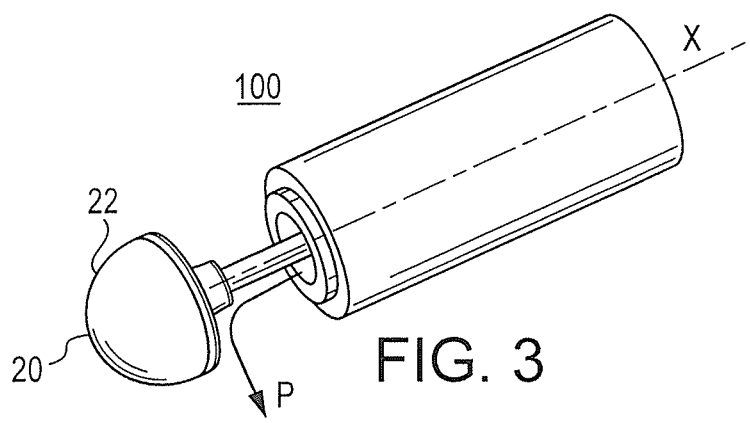
FIG. 3 shows a third embodiment, in a drawing corresponding to that in FIG. 2.

The embodiment shown in FIG. 3 differs from the embodiment in FIG. 2 in that instead of being flat, the distal section of the guiding device 20 is hemispherical, and thus as a whole constitutes a rounded contour 22 that likewise reduces the risk of injury.

The embodiments of the guiding device 20 shown in FIGS. 2 and 3 provide the same 360° arcing capabilities as described with respect to FIG. 1. In the embodiments shown in FIGS. 2 and 3, the concave inner section 21 diverts the gas/plasma in such a way to create a gas flow which extends (substantially) perpendicularly to the longitudinal axis X of the gas-delivering device/probe (e.g., in the direction represented by arrow P). As can clearly be seen in FIG. 2, the concave inner surface 21 of guiding device 20 extends to a rim (at rounded contour 22) of the guiding device 20, in a perpendicular manner relative to the longitudinal axis X of the gas-delivering device, such that the gas/plasma is directed in the direction represented by the arrow P (e.g., forming the gas flow that extends perpendicularly to the longitudinal axis X of the gas-delivering device/probe).

In any of the disclosed embodiments, the electrode 3 can be made retractable and/or can be pushed forward, out of the outlet 13, so that when the electrode 3 is in the retracted state the guiding device 20 is seated on the outlet 13. This positioning avoids the danger that during insertion of the gas-delivering device 10 or a correspondingly designed probe, body fluid or the like will enter the lumen of the gas-delivering device 10, because when in this state the outlet 13 is closed.

What is claimed as new and desired to be protected by Letters Patent of the United States is:

1. An apparatus for coagulating tissue, comprising:
   a gas-delivering device defining an outlet and adapted to deliver, in use, a plasma comprised of an ionized inert gas from the outlet of the gas-delivering device;
   an electrode adapted to supply a high-frequency current, a distal end of the electrode projecting out of the gas-delivering device; and
   a guiding device disposed at a distal end of the electrode, wherein a cross-section of at least a portion of said guiding device is at least a size of an opening of said outlet at a furthest distal end of said gas-delivering device in order to divert said plasma substantially radially with respect to an opening of said outlet of said gas-delivering device, and wherein the outlet of the gas-delivering device and the guiding device are adapted such that at least a portion of the plasma is directed to a tissue to be treated, regardless of a position of the tissue relative to a rotational position of the outlet of the gas-delivering device.

2. The apparatus of claim 1, wherein the outlet of the gas-delivering device and the guiding device are adapted such that the plasma can be directed in any direction 360° with respect to the outlet of the gas-delivering device.

3. The apparatus of claim 1, wherein when a high-frequency current is supplied to the plasma, an electric arc is formed between the electrode and the tissue to be treated.

4. The apparatus according to claim 1, wherein the outlet of the gas-delivering device and the guiding device are adapted such that the plasma is directed along a path of least electric resistance, causing the plasma to be automatically directed to the tissue to be treated.

5. The apparatus according to claim 1, wherein the guiding device is comprised of an electrically insulating material.

6. The apparatus according to claim 1, wherein the guiding device is comprised of a thermally stable material.

7. The apparatus according to claim 1, wherein the guiding device is comprised of a ceramic material.

8. The apparatus according to claim 1, wherein the guiding device defines a concave configuration on a side thereof that faces the outlet.

9. The apparatus of claim 8, wherein the concave configuration on the side of the guiding device that faces the outlet, comprises a concave surface that extends to a rim of the guiding device, in a perpendicular manner relative to a longitudinal axis of the gas-delivering device.

10. The apparatus according to claim 1, wherein the guiding device defines a rounded contour in order to prevent mechanical damage if the guiding device touches the tissue.

11. The apparatus according to claim 1, wherein the electrode is movable relative to the outlet such that when the electrode is moved into a retracted position the guiding device closes the outlet in a substantially leakproof manner.

12. The apparatus according to claim 11, wherein the entire outlet is covered by the guiding device when the guiding device is in the retracted position.

13. The apparatus of claim 1, wherein the guiding device is supported on the electrode.

14. The apparatus of claim 1, wherein the guiding device is adapted such that the plasma is directed perpendicularly relative to a longitudinal axis of the gas-delivering device.

15. The apparatus of claim 1, wherein a distal end of the guiding device is flat.

16. An apparatus for coagulating tissue, comprising:
    a gas-delivering device defining an outlet and adapted to deliver, in use, a plasma comprised of an ionized inert gas from the outlet of the gas-delivering device;
    an electrode adapted to supply a high-frequency current, a distal end of the electrode projecting out of the gas-delivering device; and
    a guiding device disposed at a distal end of the electrode, wherein a cross-section of at least a portion of said guiding device is at least a size of an opening of said outlet at a furthest distal end of said gas-delivering device in order to divert said plasma substantially radially with respect to an opening of said outlet of said gas-delivering device, and wherein the outlet of the gas-delivering device and the guiding device are adapted such that when a high-frequency current is supplied to the plasma, an electric arc can be formed in any direction 360° with respect to the outlet of the gas-delivering device.

17. The apparatus according to claim 16, wherein the outlet of the gas-delivering device and the guiding device are adapted such that the plasma is directed along a path of least electric resistance, causing the electric arc to be automatically directed to a tissue to be treated, regardless of a position of the tissue relative to a rotational position of the outlet of the gas-delivering device.

18. The apparatus according to claim 16, wherein the guiding device is comprised of an electrically insulating material.

19. The apparatus according to claim 16, wherein the guiding device is comprised of a thermally stable material.

20. The apparatus according to claim 16, wherein the guiding device is comprised of a ceramic material.

21. The apparatus according to claim 16, wherein the guiding device defines a concave configuration on a side thereof that faces the outlet.

22. The apparatus according to claim 16, wherein the guiding device defines a rounded contour in order to prevent mechanical damage if the guiding device touches the tissue.

23. The apparatus according to claim 16, wherein the electrode is movable relative to the outlet such that when the electrode is moved into a retracted position the guiding device closes the outlet in a substantially leakproof manner.

24. The apparatus of claim 16, wherein the guiding device is adapted such that the plasma is directed perpendicularly relative to a longitudinal axis of the gas-delivering device.

25. An apparatus for coagulating tissue, comprising:
a gas-delivering device defining an outlet and adapted to deliver, in use, a plasma comprised of an ionized inert gas from the outlet of the gas-delivering device;
an electrode adapted to supply a high-frequency current, a distal end of the electrode projecting out of the gas-delivering device; and
a guiding device disposed at a distal end of the electrode, wherein a cross-section of at least a portion of said guiding device is at least a size of an opening of said outlet at a furthest distal end of said gas-delivering device in order to divert said plasma substantially radially with respect to an opening of said outlet of said gas delivering device, and wherein the outlet of the gas-delivering device and the guiding device are adapted such that the plasma can be directed in any direction 360° with respect to the outlet of the gas-delivering device, the plasma being directed along a path of least electric resistance, causing the plasma to be directed to a tissue to be treated, regardless of a position of the tissue relative to a rotational position of the outlet of the gas-delivering device.

26. The apparatus of claim 25, wherein when a high-frequency current is supplied to the plasma, an electric arc is formed between the electrode and the tissue to be treated.

27. The apparatus of claim 25, wherein the guiding device is adapted such that the plasma is directed perpendicularly relative to a longitudinal axis of the gas-delivering device.

28. A tubular apparatus for coagulating tissue, the tubular apparatus having an apparatus diameter and comprising:
a gas-delivering device defining a circular outlet with an outlet diameter and adapted to deliver, in use, a plasma comprised of an ionized inert gas from the circular outlet of the gas-delivering device;
an electrode adapted to supply a high-frequency current, a distal end of the electrode projecting out of the gas-delivering device; and
a guiding device disposed at a distal end of the electrode, the guiding device having at a distal end of the guiding device circular section and at a proximal end, opposite the circular outlet, a concave inner section;
wherein the circular outlet of the gas-delivering device and the concave inner section guiding device are adapted such that at least a portion of the plasma is directed to a tissue to be treated, regardless of a position of the tissue relative to a rotational position of the circular outlet of the gas-delivering device,
wherein the electrode together with the guiding device is movable relative to the circular outlet in a longitudinal direction of the tubular apparatus such that, when the electrode is moved into a retracted position, the concave inner section of the guiding device closes the circular outlet in a substantially leak-proof manner by engaging with the circular outlet,
wherein the circular section of the guiding device has a diameter that is greater than the outlet diameter and smaller than or equal to the apparatus diameter, and
wherein the guiding device is designed such that in the retracted position the circular section is the most distal part of the tubular apparatus.

* * * * *